United States Patent [19]

Noiles et al.

[11] E Re. 28,932

[45] Reissued Aug. 17, 1976

[54] SURGICAL STAPLING INSTRUMENT

[75] Inventors: Douglas G. Noiles, New Canaan; Graham W. Bryan, Ridgefield, both of Conn.

[73] Assignee: United States Surgical Corporation, Baltimore, Md.

[22] Filed: May 8, 1975

[21] Appl. No.: 575,580

Related U.S. Patent Documents

Reissue of:

[64] Patent No.: 3,819,100
Issued: June 25, 1974
Appl. No.: 293,470
Filed: Sept. 29, 1972

[52] U.S. Cl. ..... 227/19; 227/121; 227/129

[51] Int. Cl.[2] ..... B25C 5/02

[58] Field of Search ..... 227/19, 121, 129

[56] References Cited

UNITED STATES PATENTS

| | | | |
|---|---|---|---|
| 2,275,548 | 3/1942 | Olsen | 227/121 |
| 2,801,415 | 8/1957 | Jenny | 227/130 |
| 3,618,842 | 11/1971 | Bryan | 227/19 |

*Primary Examiner*—Granville Y. Custer, Jr
*Attorney, Agent, or Firm*—Fleit & Jacobson

[57] ABSTRACT

A surgical stapling instrument for applying sterilized staples to the disunited skin or fascia of a patient in order to effect a joining of the skin or fascia. The instrument is adapted to associate with a staple-carrying cartridge having a plurality of staples therein. The instrument is manually powered and includes a nose portion rotatably mounted in a hand-held main body portion and adapted to mount the staple-carrying cartridge so that the stapling angle can be varied without rotating the hand-held portion of the stapler. A clutch means is provided for ensuring that the staple-advancing drive means of the instrument is only activated once per stapling operation. The instrument is further provided with means for preventing the insertion of a fresh staple-carrying cartridge until the instrument is in the readiness position for a driving stroke, and means for maintaining the unloaded instrument in its readiness position until equipped with a cartridge.

22 Claims, 22 Drawing Figures

SURGICAL STAPLING INSTRUMENT

Matter enclosed in heavy brackets [ ] appears in the original patent but forms no part of this reissue specification; matter printed in italics indicates the additions made by reissue.

BACKGROUND OF THE INVENTION

In U.S. Pat. No. 3,643,851, assigned to the present assignee and entitled SKIN STAPLER, there is disclosed a surgical stapler for joining the disunited skin of a patient. The surgical stapler disclosed in this commonly assigned patent employs a staple-carrying cartridge comprising an anvil adapted to lie flush with the skin, a plurality of staples which are to be folded around the anvil, and a pusher for ejecting and bending the staples around the anvil. The surgical stapling instrument adapted to accept the staple-carrying cartridge in this commonly assigned patent is powered by a pressurized gas. Later developments of the gas-powered stapler and cartridges for applying surgical staples to external skin and internal fascia are disclosed in U.S. Pat. No. 3,662,939, assigned to the present assignee and entitled "SURGICAL STAPLER FOR SKIN AND FASCIA."

Although these gas-powered instruments represent a marked advance over the state-of-the-art, there are certain disadvantages associated with the use of gas-powered units of this type. One of the obvious disadvantages is the necessity for replacing the gas cartridges after their contents have been exhausted, and a second is the inconvenience associated with storing and maintaining a supply of these cartridges. Also, the powering mechanism is complex, is hence somewhat costly, and comprises numerous close-tolerance elements which tend to be susceptible to malfunction. For these and other obvious reasons, it would be advantageous to have a simple surgical stapling instrument adapted to accept staple-carrying cartridges of the type disclosed in the above commonly assigned patents, but which is powered manually and without the intervention of a gaseous medium and the disadvantages associated therewith.

Accordingly, it is a broad object of the present invention to provide a surgical stapling instrument for stapling the disunited skin or fascia of a patient which is manually powered and wholly operated by mechanical means.

It is another object of the present invention to provide a surgical stapler in which the staple-carrying cartridge is mounted so that it is rotatable relative to the hand-held main body portion of the instrument so that the staples can be applied at any angle without the necessity for rotating the hand-held portion of the instrument.

It is yet another object of the present invention to provide a surgical stapler with means for ensuring that the staple-advancing drive means of the instrument is activated only once in each stapling operation.

Another object of the invention is to provide means for preventing a driving stroke of a surgical stapler absent the association with a staple-carrying cartridge.

It is yet a further object of the present invention to provide means for preventing the insertion of a staple-carrying cartridge into the surgical stapler until the driving mechanism of the stapler has been returned to its initial position.

It is still a further object of the present invention to provide a surgical stapler with means to alert the surgeon when a staple has been advanced into the ready position and is about to be ejected and formed.

These and other objects of the invention, as well as many of the attendant advantages thereof, will become more readily apparent when reference is made to the following description taken in conjunction with the accompanying drawings.

SUMMARY OF THE INVENTION

The present invention relates to a surgical instrument for stapling together disunited segments of the external skin or internal fascia of a patient.

The surgical stapling instrument generally comprises a main body portion having a nose portion rotatably mounted therein and adapted to receive and mount a staple-carrying cartridge. The nose portion of the stapler houses the drive means for advancing and forming the staples. A pusher-activating means for driving the pusher element of the staple-carrying cartridge to eject and form the staples around the anvil means of the cartridge comprises a thrust bar slidably mounted for reciprocative movement in the nose portion of the stapler. The thrust bar is attached to and adapted to move with a collar element slidably mounted on the nose portion of the stapler. A trigger means comprises a handle which is pivotally mounted on the main body portion of the stapler and has means for engaging the collar element so that the thrust bar is moved forwardly by squeezing the trigger. A return spring attached to the trigger and to the main body portion of the stapler functions to return the thrust bar to its initial position after the thrust stroke of the bar has been completed.

The drive means to activate the staple-advancing means in the staple-carrying cartridge for driving the staples toward the anvil comprises pinion gears and pinion shafts also housed within the nose portion of the stapler. The teeth of the pinion gears mesh with the teeth of a main gear which is adapted to rotate in unison with a ratchet. The main gear and ratchet are rotatably mounted in the rear nose portion of the stapler. An index pawl pivotally attached to the thrust bar and operatively associated with the ratchet causes the ratchet, main gears and pinions to rotate when the thrust bar is initially moved forward and thus activates the staple-advancing means in the cartridge.

As was the case in the above-referenced commonly assigned patents, it is desirable to rotate the particular drive screws of the staple-carrying cartridge 360° each time a staple is being ejected by first over-driving and then return-driving the screws. Accordingly, and similar to the gear boxes disclosed in the commonly assigned patents, the drive means for advancing staples of the present invention is adapted to be over-driven and then returned to a position wherein the drive screws of the cartridge are rotated exactly 360°. The return movement of the staple-advancing drive means is accomplished by a spring pawl which cooperates with the above-mentioned ratchet. This spring pawl also functions as a stop preventing excessive return rotation of the ratchet.

Means are also provided for preventing more than one staple from being placed in the ready position of the staple-carrying cartridge during the stapling operation. This means comprises a clutch means which prevents the return of the thrust bar to its initial position until it has completed a full stroke, thereby ejecting a staple from the staple-carrying cartridge. The clutch means includes a cam block mounted in the forward end of the nose portion of the stapler and having an inclined surface facing the thrust bar. The forward end of the thrust bar passes through the cam block and operatively engages a cylindrical roller positioned between the thrust bar and the inclined surface of the cam block. The cam block houses a spring-biased wedge which cooperates with the cylindrical roller. The cooperation between these elements is such that the cylindrical roller prevents the thrust bar from being returned to its initial position until it has completed a full driving thrust movement.

Means are further provided for preventing the forward movement of thrust bar until a staple-carrying cartridge has been mounted on the stapler. This means comprises a cartridge interlock housed in the forward end of the nose portion of the stapler and spring-biased into a position such that it blocks the forward movement of the thrust bar until a cartridge is properly mounted. In its initial position, the forward end of the thrust bar abuts the rear face of the cartridge interlock. When the staple-carrying cartridge is mounted, the cartridge interlock is forced upward by the staple-carrying cartridge thereby registering an opening in the cartridge interlock with the forward end of the thrust bar such that the thrust bar is capable of being moved forward and driving the pusher element of the staple-carrying cartridge to eject and form the staples.

The forwardmost staple in the staple-carrying cartridge is advanced into the ready position during the initial stage of the forward thrust stroke of the thrust bar. At this point and with the thrust bar partially advanced, it is possible to remove the staple-carrying cartridge from the stapler. Under these circumstances, the clutch means prevents the thrust bar from returning to its initial position. Accordingly, the thrust bar must be fully advanced before it will be automatically returned to its initial position. The surgeon or his attendant may not remember to follow this procedure, however, and may attempt to mount a staple-carrying cartridge in the stapler while the thrust bar is in this partially advanced position. This procedure could result in jamming the drive mechanisms of the staple-carrying cartridge or other undesirable mechanical difficulty.

To prevent such jamming, means are provided for preventing a cartridge from being mounted unless the thrust bar has returned to its initial position. This means comprises a cartridge stop lock mounted in the forward end of the nose portion of the stapler. When the thrust bar is in its initial position, the cartridge stop lock is oriented so that a staple-carrying cartridge can be easily locked in the stapler. If the thrust bar is not in its initial position, however, but rather is in a partially advanced position, the cartridge stop lock is spring-biased into a blocking position so that a staple-carrying cartridge cannot be fully mounted in the stapler.

While the initial movement of the trigger advances the staples and the intermediate movement readies the cartridge for the stapling operation, only the final stages of trigger movement effect the ejection and formation of a staple. Accordingly, it is desirable to alert the surgeon to the fact that a staple is about to be ejected so that the surgeon can be sure that the instrument is properly positioned. In fact, the inventive instrument could be operated remote from the patient until the last stage of trigger movement, and only then oriented in readiness for a stapling operation. As part of the present invention, the stapler is provided with a spring-biased wedge housed in the nose portion of the stapler which snaps into a notch on the top surface of the thrust bar with an audible "click" just before a staple is to be ejected. At the same time, the surgeon will also feel a slight but noticeable change in the force required to squeeze the trigger, thus further alerting him to the fact that a staple is about to be ejected.

As just described, the drive means for advancing staples in the staple-carrying cartridge and for ejecting staples therefrom are housed in the nose portion of the stapler which is rotatably mounted in the main body portion. Since the staple-carrying cartridge is mounted in the nose portion and rotatable therewith, it is possible to change the stapling angle of the stapler by merely rotating the nose portion while maintaining the hand-held main body portion in a fixed position.

DETAILED DESCRIPTION OF THE INVENTION

Figure 1:
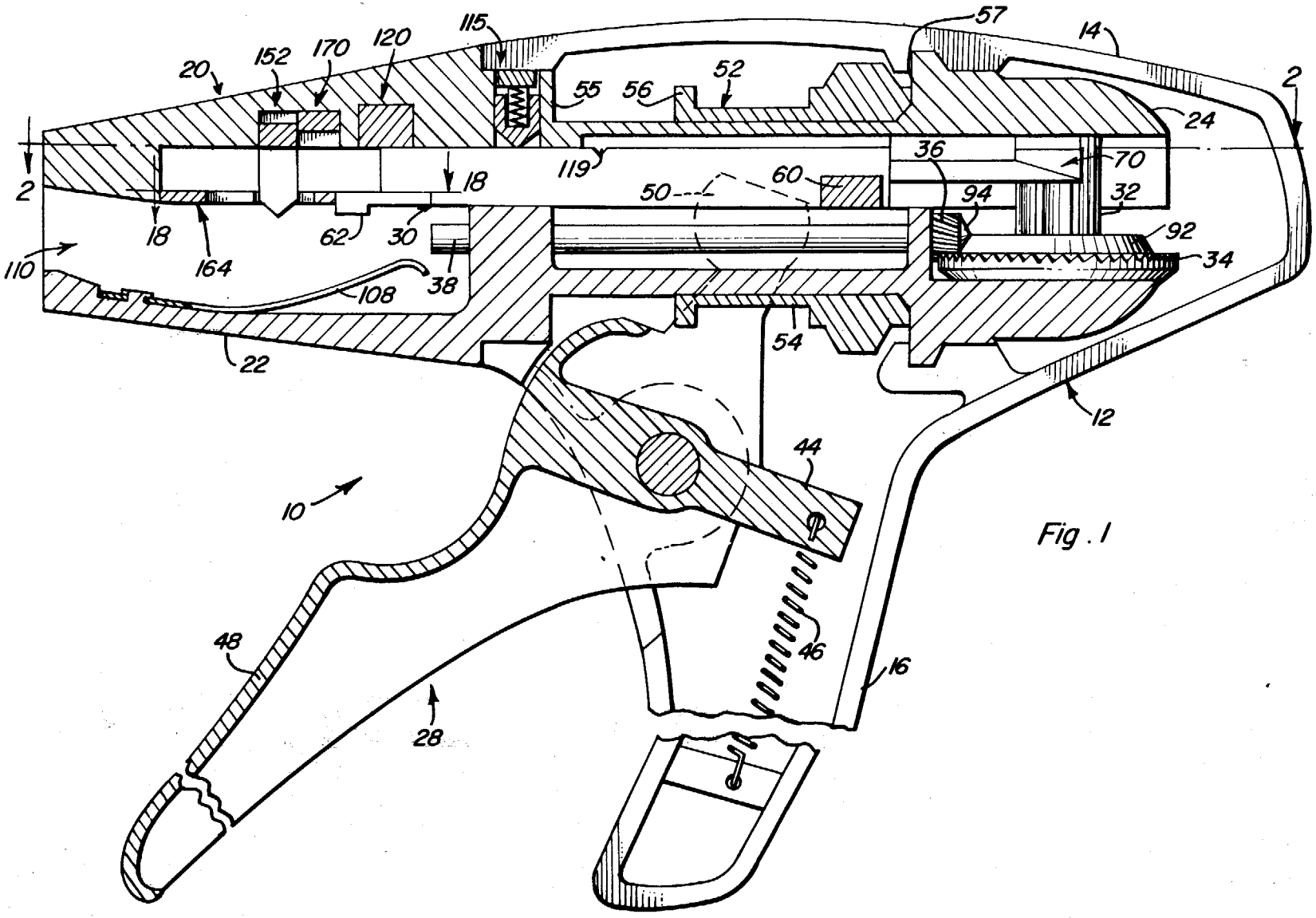
FIG. 1 is a vertical cross-section of the surgical stapling instrument of the present invention.

With reference first to FIGS. 1–6, the surgical stapler of the present invention will be described in general terms. The stapler shown generally at 10 comprises housing 12 having main body portion 14 and handle portion 16. Nose portion 20 of stapler 10 is rotatably mounted in main body portion 14 of housing 12. Nose portion 20 includes a front section 22 extending out of housing 12 and adapted to mount staple-carrying cartridge 26. Nose portion 20 further includes a rear section 24 located inside housing 12 and acting to house the driving means for advancing, ejecting and forming staples from the staple-carrying cartridge. Nose portion 20 is conveniently formed in two parts, upper and lower, held together by a pair of screws 21 and held in relative alignment by dowel pins 23 and 25. Staple-carrying cartridge 26 is shown fitted into nose portion 20 of stapler 10 in FIG. 6.

The staples in staple-carrying cartridge 26 are advanced, ejected and formed by mechanical means only and without the intervention of a gaseous medium. Accordingly, the power for advancing, ejecting and forming the staples in cartridge 26 comes from the manipulative force supplied to stapler 10 by the surgeon. This force is transmitted to the drive means of stapler 10 by means of trigger 28 which generally comprises a handle pivotally attached to housing 12. Pivoting of trigger 28 causes a thrust bar 30, the pusher-activating means, to drive the pusher element of staple carrying cartridge 26 forward to eject and form a staple around the anvil means. At the same time, a [ pusher-engaging ] *ratchet* 32 and a main gear 34 housed in the rear portion 24 of nose 20 are caused to rotate. Main gear 34 in turn rotates a pair of pinion gears 36 and pinion shafts 38 which associate with the cartridge 26 to advance the staples.

Figures 4, 5, 6:
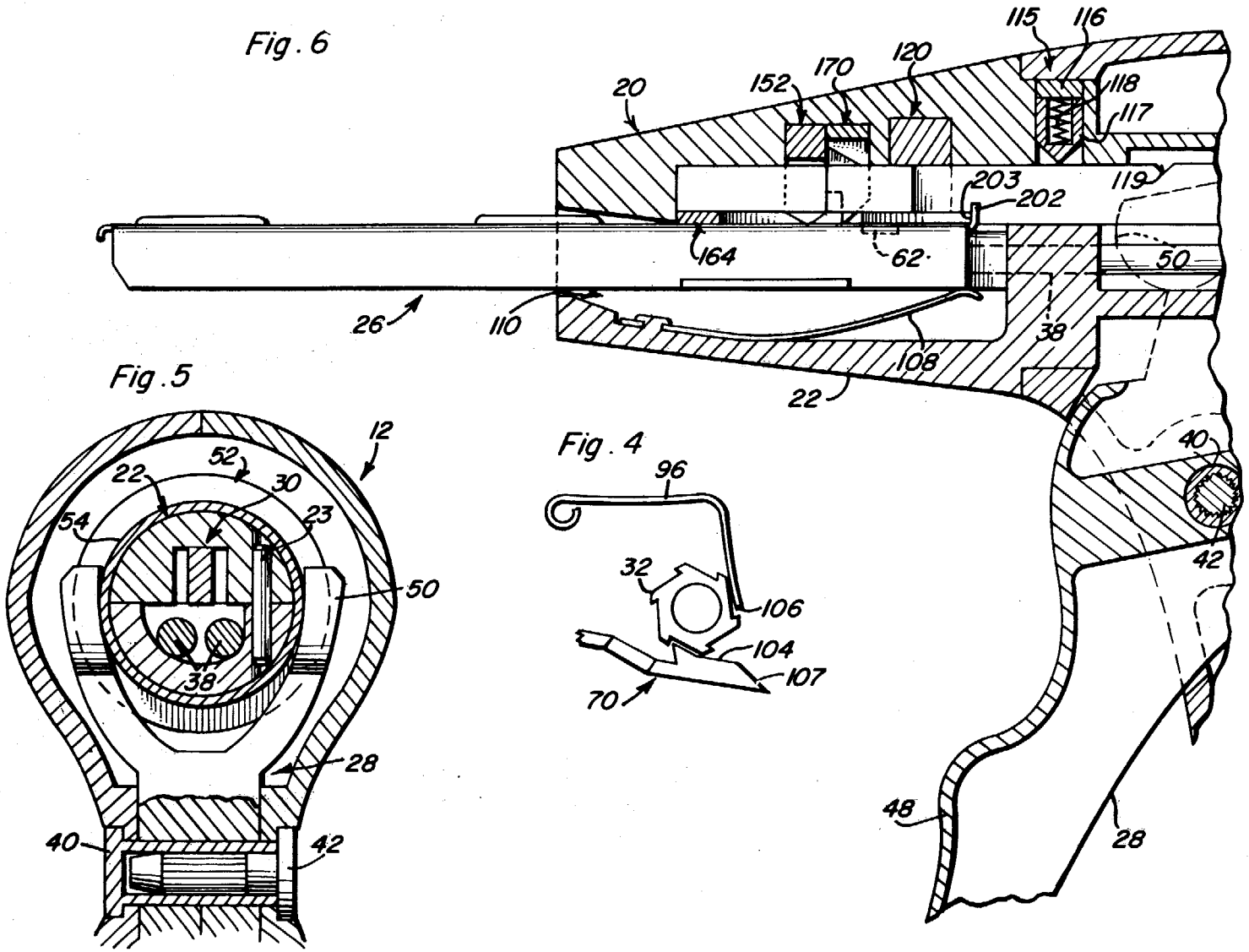
FIG. 4 is a horizontal, fragmentary view of a portion of the staple-advancing drive mechanism of the stapler during the stapling operation.
FIG. 5 is a vertical cross-section of the stapler looking rearwardly.
FIG. 6 is a side view, partially in section, of the staple-carrying cartridge mounting portion of the stapler after the cartridge is mounted and ready for use.

With reference now to FIGS. 1 and 5, trigger 28 will be described. Trigger 28 is pivotally mounted to housing 12 by means of stud 40 and drive pin 42. Trigger 28 is of appropriate size and shape to be conveniently gripped by the operating hand of a surgeon. The trigger includes a rearward extending portion 44 to which is attached one end of a return spring 46. The other end of return spring 46 is attached to housing 12 and functions to return trigger 28 and thrust bar 30 to their initial positions after staple forming has occurred. Trigger 28 is of Y-shape and includes a lower hand-engaging portion 48 and an upper force-transmitting yoke portion 50. Yoke 50 embraces a collar 52 slidingly mounted around the mid-section of nose portion 20 and adapted to rotate therewith. Collar 52 includes a cylindrically-shaped body member 54 having outwardly and radially extending flange portions 56 at each end. Yoke 50 is positioned around cylindrically-shaped body member 54 and between the flange portions 56. Shoulder portions 55 and 57 of nose portion 20 limit the forward and rearward movement, respectively, of collar 52. Pivoting of trigger 28 results in longitudinally directed force being exerted on collar 52 by yoke portion 50 of trigger 28. Accordingly, when the trigger is activated, collar 52 simultaneously slides along the mid-section of nose 20. Also, by this arrangement, collar 52 is free to rotate relative to trigger 28.

Figure 2:
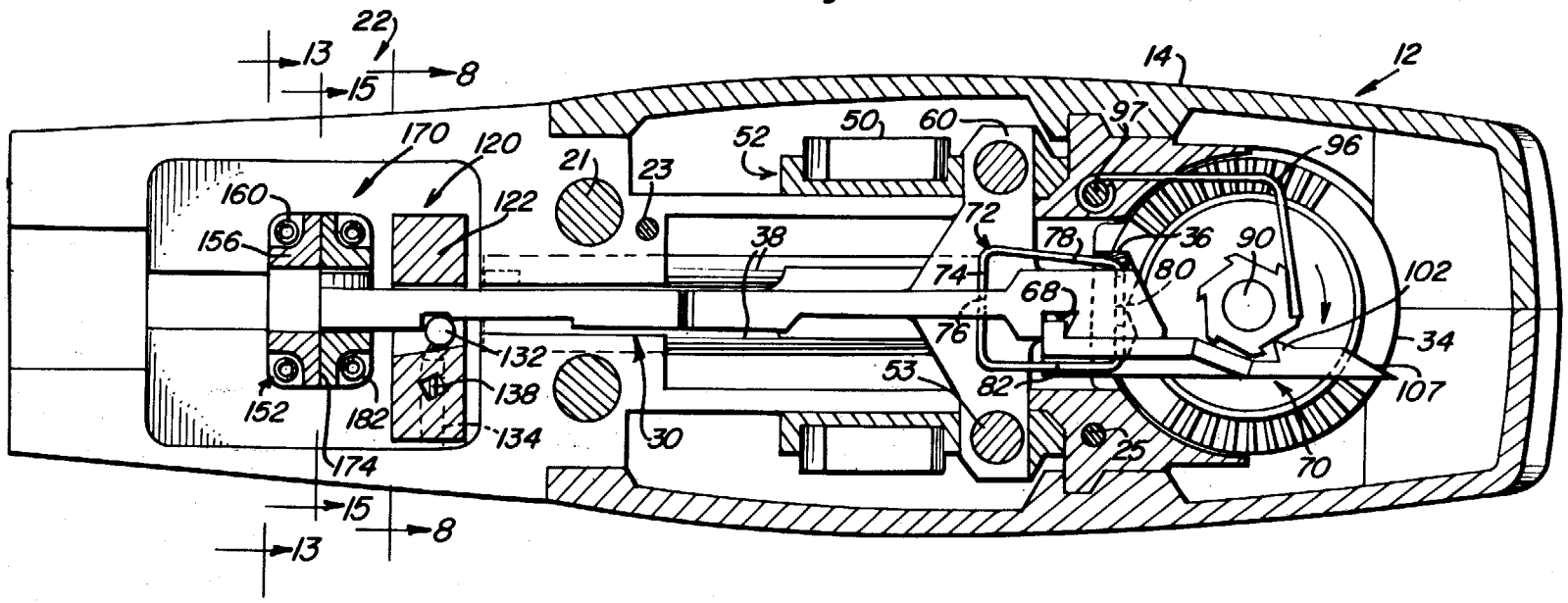
FIG. 2 is a horizontal cross-section taken along line 2—2 of FIG. 1.
Figure 3:
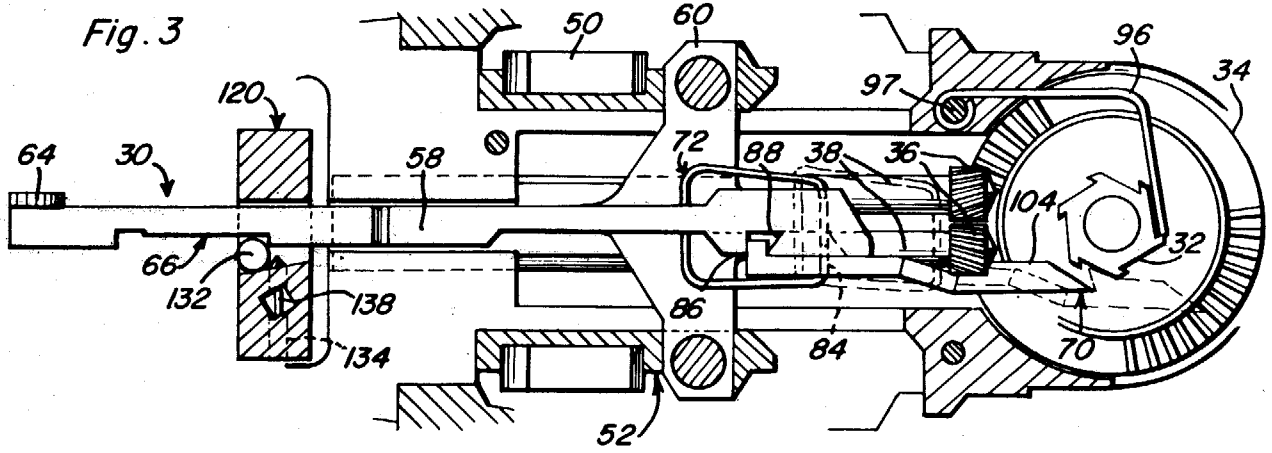
FIG. 3 is similar to FIG. 2 but shows a portion of the stapler during the stapling operation.
Figure 17:
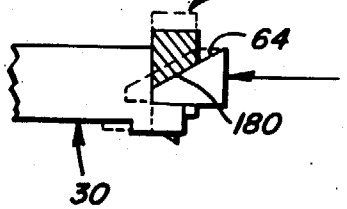
FIG. 17 shows the cooperation between the inclined surfaces of the thrust bar and cartridge stop lock.
Figure 19:
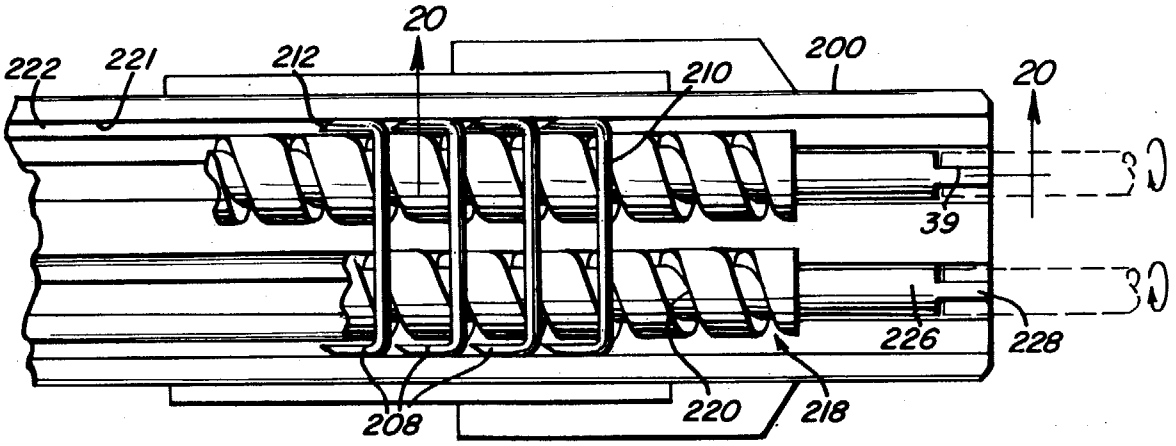
FIG. 19 is an enlarged view of the rear portion of a staple-carrying cartridge with its cover removed.
Figure 20:
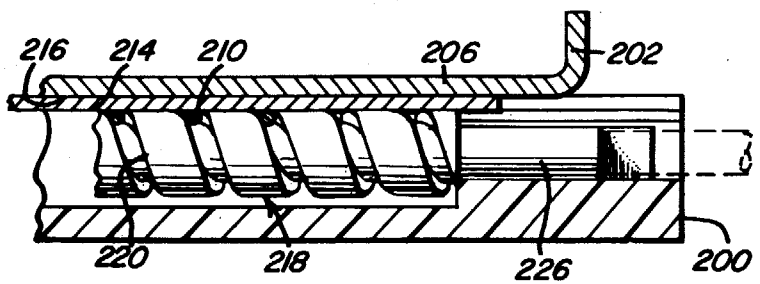
FIG. 20 is a cross-section taken along line 20—20 of FIG. 19.
Figure 21:
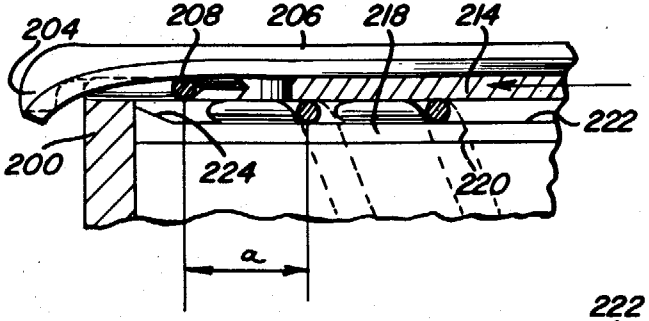
FIG. 21 is a vertical cross-section of the front portion of a staple-carrying cartridge.

As best seen in FIGS. 1, 3 and 17, the means for driving the pusher element of the staple-carrying cartridge to eject and form staples comprises thrust bar 30 which includes an elongated central section 58 having a wing portion 60 near the rear end thereof. A pusher-engaging extension 62 and an inclined surface 64 are positioned at the forwardmost end of thrust bar 30. Inclined surface 64 is adapted to engage a stop lock mechanism which will be discussed subsequently. Also located near the front end of thrust bar 30 is an elongated notch 66 which forms a part of the clutch means of the present invention. Located near the rear end of thrust bar 30 is a second notch 68 which engages the forward end of index pawl 70. Thrust bar 30 is slidingly mounted in nose portion 20 and is adapted to rotate therewith. As illustrated in FIG. 2, wing portion 60 of thrust bar 30 lies near the mid-section of collar 52, conveniently formed as two semi-circular parts, and is rigidly attached to collar 52 by means of bolts 53. Accordingly, thrust bar 30 reciprocates back and forth with collar 52 when trigger 28 is pivoted, and collar 52 rotates with thrust bar 30 when nose portion 20 is rotated.

The staple-advancing drive means of the stapler 10 is arranged so that when thrust bar 30 is moved forward, the elements forming a part of this arrangement are activated. That is, the forward motion of the pusher-activating element causes the rotation of the screws of staple-carrying cartridge 26 thereby advancing the staples. And as will be more fully described below, the staples are slightly over-driven during the forward stroke of thrust bar 30 and are then returned to their proper positions as will be discussed subsequently.

With reference now to FIGS. 1–4, the staple-drive mechanism will be explained. The index pawl 70 is pivotally attached to the rear end of thrust bar 30. The transverse base portion 74 of spring 72 passes through aperture 76 in thrust bar 30 and the inturned end of upstanding leg 78 of spring 72 fits into one end of an aperture 80 in the rear end of thrust bar 30 and the inturned end of upstanding leg 82 fits through an aperture 84 in index pawl 70 and then into the other end of aperture 80 in thrust bar 30. An upstanding leg 86 on the forward end of index pawl 70 fits into notch 68 in thrust bar 30. Notch 68 is trapezoidal in shape and has inclined surface 88. The combination of spring 72 and inclined surface 88 of notch 68 allows index pawl 70 to pivot outwardly.

Index pawl 70 rides along on wall of a six-tooth ratchet 32 and engages one of the teeth thereof. The index pawl, pivotally mounted on thrust bar 30, is biased toward ratchet 32 by spring 72. Ratchet 32 is attached to, and rotates with, a main gear 34. Ratchet 32 and main gear 34 are of unitary construction, as illustrated, and are rotatably mounted in the rear end 24 of nose portion 20 by means of shaft 90. The teeth of main gear 34 mesh with the teeth of two pinion gears 36, both of which are seen in the drawings. Pinion gears 36 are in turn attached to pinion shafts 38 which are housed in, and extend longitudinally through, the nose portion 20 of stapler 10. A tapered cylindrical body portion 92 on the ratchet 32 and main gear 34 assembly provides a stop for pinion gears 36 which have a rear portion 94 which abuts body portion 92 of the ratchet 32 and main gear 34 assembly. (See FIG. 1). This arrangement prevents the pinion shafts from inadvertently being moved out of their proper longitudinal position.

Thrust bar 30, index pawl 70 and ratchet 32 are arranged in such a manner that the forward stroke of thrust bar 30 causes ratchet 32 and accordingly main gear 34 to move slightly more than 60°. As noted previously, it is desired to ultimately rotate the screws associated with staple-carrying cartridge 26 precisely 360° for each staple driving operation. The staple-advancing drive means in stapler 10 is arranged so that for each 60° turn of ratchet 32 and main gear 34, pinion shafts 38 and the screws in cartridge 26 are rotated 360°. However, to ensure that the staples are advanced a proper amount, it has been found desirable to overdrive the screws in cartridge 26 and thus the staples, and then to reverse the rotation of the screws so that ultimately they experience a net 360° rotation. It is for this reason that six-tooth ratchet 32 is rotated slightly more than 60°. It becomes necessary therefore to provide means for returning ratchet 32 to its 60° position. The ratchet return is brought about by means of spring pawl 96 as will be discussed subsequently.

With particular reference now to FIGS. 2–4, the operation of the drive means for activating the staple-advancing mechanism of the staple-carrying cartridge and for driving the staples toward the anvil will be described. As shown in FIG. 2, thrust bar 30 is in its initial at rest position. In this position, index pawl 70 is in engagement with ratchet 32. Tooth portion 102 of index pawl 70, which is the driving region thereof, is removed from the nearest tooth on ratchet 32 to allow for slight "play" before the ratchet 32 is rotated.

When thrust bar 30 moves forward, during a stapling operation, index pawl 70 rotates ratchet 32. Ratchet 32 is rotated in a clockwise direction as index pawl 70 is moved forward with thrust bar 30. When ratchet 32 has been rotated through approximately its desired maximum angle of slightly greater than 60°, the back surface of an advancing tooth of ratchet 32 engages planar portion 104 near the end of index pawl 70 and forces tooth portion 102 of index pawl 70 out of engagement with ratchet 32 (See FIG. 4). The maximum angle through which ratchet 32 is rotated is greater than that needed to advance each staple one "staple unit." Thus, the staple-advancing drive means is momentarily overdriven; however, this condition is automatically corrected by spring pawl 96.

Referring now to FIGS. 2 and 4, it can be seen that spring pawl 96 is attached to the rear end 24 of nose portion 20 by means of a pin 97 and comprises an arcuate section terminating at end 106. Spring pawl 96 contacts ratchet 32 at two points in its initial position. First, end 106 of spring pawl 96 contacts one of the teeth of ratchet 32. Second, a point on spring pawl 96 partially between end 106 and the arcuate section contacts the back surface of the adjacent tooth. Accordingly, when ratchet 32 is momentarily over-driven, spring pawl 96 is cammed outward as shown in FIG. 4; however, ratchet 32 is then immediately returned to an exactly 60° rotation by the biasing action of spring pawl 96. It will be noted that the counterclockwise rotation of ratchet 32 terminates when end 106 of spring pawl 96 contacts a tooth on ratchet 32. Accordingly, when thrust bar 30 and index pawl 70 are in the fully advanced position, shown in solid lines in FIG. 3, spring pawl 96 has the same relationship to ratchet 32 as it did when thrust bar 30 and index pawl 70 were in their initial positions illustrated in FIG. 2.

After the forward thrust of thrust bar 30 has been completed and a staple ejected from the cartridge and formed in the patient, return spring 46 returns thrust bar 30 to its initial position. During this phase of operation, the end portion 106 of spring pawl 96 prevents counterclockwise rotation of ratchet 32. At the stage of the thrust bar return stroke when sloped surface 107 on index pawl 70 contacts a tooth on ratchet 32, the index pawl begins to be cammed against the force of spring 72. Further camming action then occurs when the tooth portion 102 of index pawl 70 contacts the backside of a tooth of ratchet 32. At this stage, index pawl 70 is pivoted outwardly into the position shown in phantom lines in FIG. 3. This outward pivotal movement is permitted by spring 72 and the inclined surface 88 of notch 68 of thrust bar 30. Finally, index pawl 70 reassumes the position shown in FIG. 2. At this point, stapler 10 is ready for another firing.

As previously stated, it is desirable to alert the surgeon to the fact that a staple is about to be ejected and formed so that the surgeon can be sure that cartridge 26 is properly positioned to effect a neat suture. This is accomplished by means of spring-biased means 115 housed in nose portion 20 of stapler 10. Spring-biased means 115 comprises an upper U-shaped member 116 which bears against housing 12 and a lower member 117 terminating in a V-shaped point which rides along the top of thrust bar 30. Members 116 and 117 are spring-biased apart by a coil spring 118. A notch 119 is provided on the top surface of thrust bar 30, in alignment with member 117, and is adapted to receive the V-shaped pointed end of member 117 at a stage of the stapling operation just before a staple leaves the cartridge. At this stage, member 117 is snapped into notch 119 on the top surface of thrust bar 30 by spring 118 with an audible "click." Further movement of thrust bar 30 in the forward direction forces member 117 upward against the force of spring 118 so that thrust bar 30 can continue its forward movement. This sequence of events will also cause the surgeon to feel a slight but noticeable change in the force required to squeeze the trigger, thus further alerting him to the fact that a staple is about to be ejected. Member 116 also functions to provide additional frictional resistance between housing 12 and nose portion 2 to avoid uncontrolled rotation between nose portion 20 and housing 12 during normal handling and use.

Figure 8:
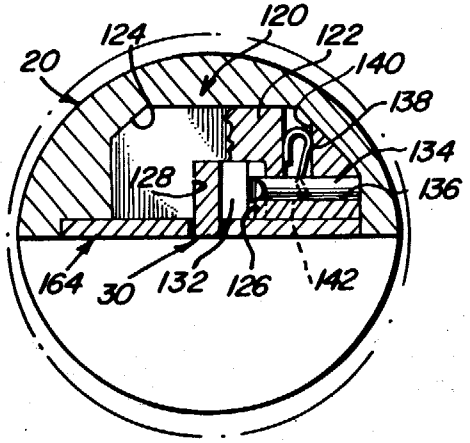
FIG. 8 is a vertical cross-section taken along line 8—8 of FIG. 2 and showing the clutch means.
Figure 7:
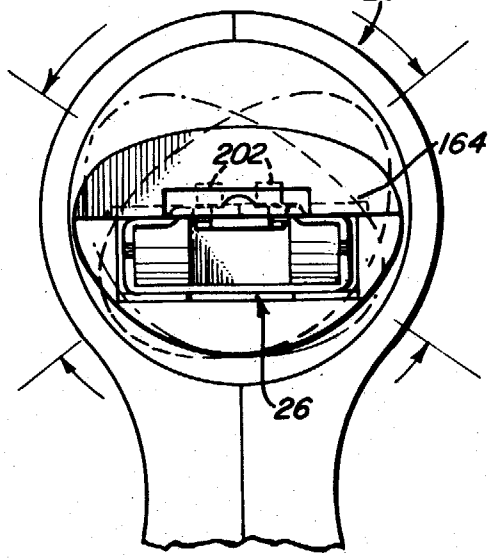
FIG. 7 is a front view of the stapler with the staple-carrying cartridge mounted and ready for use.

Turning now to FIG. 8, there is illustrated an end view of a clutch means 120. Clutch means 120 includes a cam block 122 mounted in an opening 124 in forward end 22 of nose portion 20. Cam block 122 has an inclined surface 126 facing thrust bar 30 which passes through an opening 128 in cam block 122. Inclined surface 126 is positioned relative to thrust bar 30 such that the spacing 130 between inclined surface 126 and thrust bar 30 increases in the forward thrust direction of the thrust bar. A cylindrical cam roller 132 is positioned between inclined surface 126 of cam block 122 and thrust bar 30. An elongated wedge pin 134 is housed in an aperture 136 in cam block 122. The forward end of wedge 134 is V-shaped and extends into opening 130 between inclined surface 126 and thrust bar 30. The wedge pin 134 is spring-biased toward thrust bar 30 by means of a spring 138 housed in a recess 140 in cam block 122. Recess 140 lies perpendicular to aperture 136 and the end of spring 138, which is hook-shaped, is seated in a bore 142 through wedge 134. Cam roller 132 lies adjacent elongated notch 66 in thrust bar 30 and its movement is confined by notch 66 as will be discussed subsequently. The cooperation between these elements is such that cylindrical roller 132 prevents thrust bar 30 from being returned to its initial position until completion of a full thrust stroke.

Figure 9:
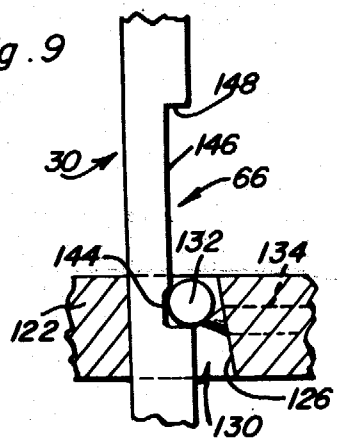

FIGS. 9–12 are sequential views showing the operation of clutch means 120 during a stapling operation. Turning first to FIG. 9, thrust bar 30 is shown in its initial position. In this position, cam roller 132 lies in a shallow cut-out 144 positioned at the forwardmost end of notch 66. Cam roller 132 is positioned in the narrowest part of opening 130 and at the rear of clutch means 120. Spring-biased wedge pin 134 maintains the cam roller 132 toward the rear end of clutch means 120.

Figure 10:
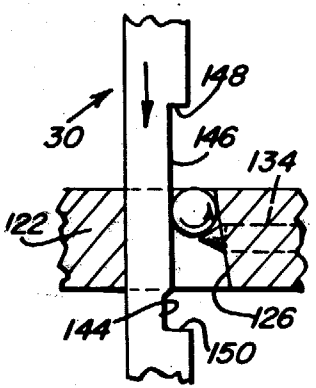

Turning now to FIG. 10, the clutch means 120 is illustrated during the forward stroke of thrust bar 30. Cam roller 132 is shown rotating in a counterclockwise direction. During this stage of thrust, the surface of cam roller 132 contacts base 146 of notch 66 and inclined surface 126, and is rotated by the movement of thrust bar 30. This rotational movement is permitted since cam roller 132 is in effect rotating "downhill" toward the widest part of opening 130. At the same time, cam roller 132 bears against spring-biased wedge 134 which restrains the longitudinal forward movement of cam roller 132 so that the cam roller is kept in the narrowest part of opening 130.

Still referring to FIG. 10, it can be seen that an attempted return movement of thrust bar 30 to its initial position from its partially advanced position would cause cam roller to rotate in a clockwise direction. This movement is not permitted by clutch means 120, however, since clockwise rotation of cam roller 132 causes cam roller 132 to "lock" itself between thrust bar 30 and inclined surface 126 of cam block 122 thereby preventing all but the slightest movement of thrust bar 30 toward its initial position. This occurs because cam roller 132 is in effect rotating "uphill" toward the narrowest part of opening 130. Furthermore, cam roller 132 would no longer be bearing against spring-biased wedge 134.

Figure 12:
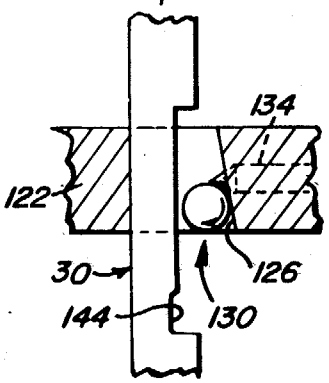
FIGS. 9–12 are sequential views showing the operation of the clutch means during a stapling operation.
Figure 11:
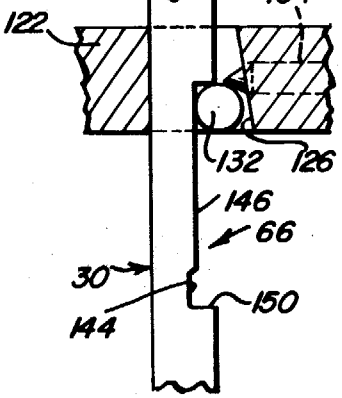

Turning now to FIG. 11, clutch means 120 is seen at the forward end of the stroke of thrust bar 30. In this position, cam roller 132 has been forced to the other side of wedge pin 134 by shoulder porton 148 of notch 66 and lies in the widest region of opening 130. Once cam roller 132 has so passed wedge 134, it is housed in an area wider than its diameter and hence is free to rotate in any direction. Accordingly, cam roller 132 permits thrust bar 30 to move rearward toward its initial position. A portion of this operational sequence is shown in FIG. 12 illustrating thrust bar 30 during its return stroke. Here, base portion 146 of notch 66 of thrust bar 30 may still lightly contact cam roller 132. However, cam roller 132 can freely rotate since opening 132 is sufficiently wide at this location. Near the end of the return movement of thrust bar 30 to its initial position, cam roller 132 is moved into cut-out 144 in notch 66 and is then forced past wedge 134 by shoulder portion 150 of notch 66. Cut-out portion 144 allows cam roller 132 to be moved past wedge 134 and back to its initial position shown in FIG. 9, without "locking" before the completion of the return stroke.

Figure 13:
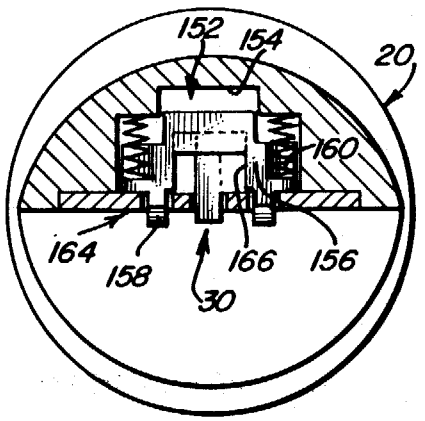
FIG. 13 is a vertical cross-section taken along line 13—13 of FIG. 2 and showing the position of the cartridge interlock before the staple-carrying cartridge is inserted.
Figure 14:
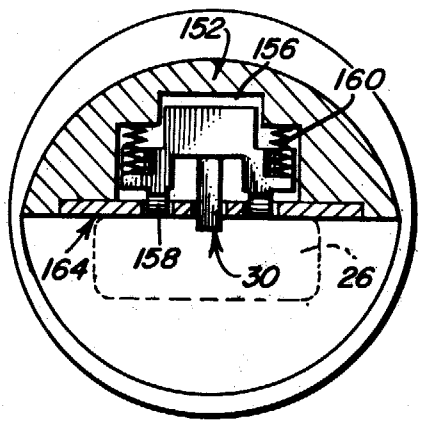
FIG. 14 is similar to FIG. 13 but shows the cartridge interlock after the insertion of the staple-carrying cartridge which is shown in phantom lines.

Turning now to FIG. 13, there is shown an end view of a cartridge interlock 152 in its initial blocking position which prevents the initiation of a thrust stroke until a cartridge is properly installed on the stapler. Cartridge interlock 152 lies in blocking and abutting relationship with the forwardmost end of thrust bar 30 when thrust bar 30 is in its initial position. Cartridge interlock 152 is positioned in an opening 154 in the forward end 22 of nose portion 20 and comprises a body portion 156 and leg portions 158. As shown in FIG. 13, cartridge interlock 152 is spring-biased into its initial blocking position by a pair of coil springs 160. In this position, leg portions 158 of cartridge interlock means 152 extend through openings 165 in a location plate 164. When a cartridge 26 is mounted on the stapler 10 as shown in FIG. 6, cartridge interlock 152 is forced upward against the action of springs 160 and into the position illustrated in FIG. 14. In this position, opening 166 in cartridge interlock 152 registers with thrust bar 30 and allows thrust bar 30 to pass therethrough. Accordingly, cartridge interlock 152 is in the position shown in FIG. 13 when a cartridge is absent and thrust bar 30 is in its initial position, and is in the position shown in FIG. 14 the remainder of the time.

Figure 15:
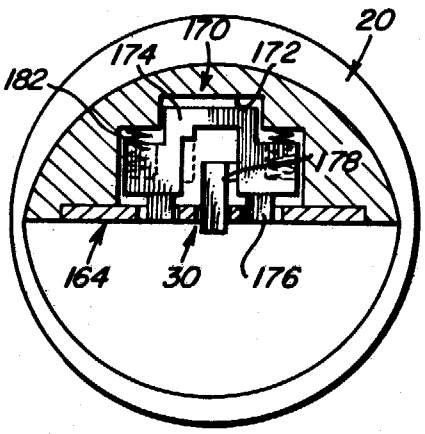
FIG. 15 is a vertical cross-section taken along line 15—15 of FIG. 2 and showing the position of the cartridge stop lock before the thrust bar has been advanced.

Referring now to FIG. 15, there is shown an end view of a cartridge stop lock 170 in its initial position. Cartridge stop lock 170 is adapted to prevent the mounting of a staple-carrying cartridge 26 in stapler 10 unless thrust bar 30 is in its fully retracted initial position. Cartridge stop lock 170 is mounted in an opening 172 in forward end 22 of nose portion 20. The cartridge stop lock 170 comprises a body portion 174 and leg portions 176. Opening 178 in cartridge stop lock 170 registers with thrust bar 30 when thrust bar 30 is in its initial position. In the position shown in FIG. 15, leg portions 176 are retracted above the bottom of location plate 164. Accordingly, staple-carrying cartridge 26 can be easily mounted on stapler 10.

Figure 16:
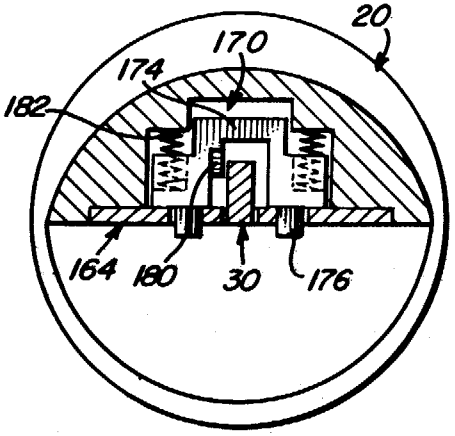
FIG. 16 is similar to FIG. 15 but shows the cartridge stop lock after the thrust bar has been partially advanced.

As best seen in FIG. 17, the cartridge stop lock 170 is held in its initial position by the inclined surface 64 of thrust bar 30 which engages a correspondingly inclined surface 180 of cartridge stop lock 170 when thrust bar 30 is in its initial position. After thrust bar 30 has left its initial position and is in the thrust or return portion of its stroke, cartridge stop lock 170 is spring-biased downward by a pair of coil springs 182 and into the position shown in FIG. 16. In this position, leg portions 176 extend through openings 184 in location plate 164 and below the bottom thereof to prevent the mounting of staple-carrying cartridge 26 until thrust bar 30 has been returned to its initial position. The return of thrust bar 30 to its initial position. The return of thrust bar 30 to its initial position causes cartridge stop lock 170 to be forced upward against the action of springs 182 as best shown in FIG. 17, wherein the initial position of thrust bar 30 and stop lock cartridge 170 are shown in phantom lines.

Figure 18:
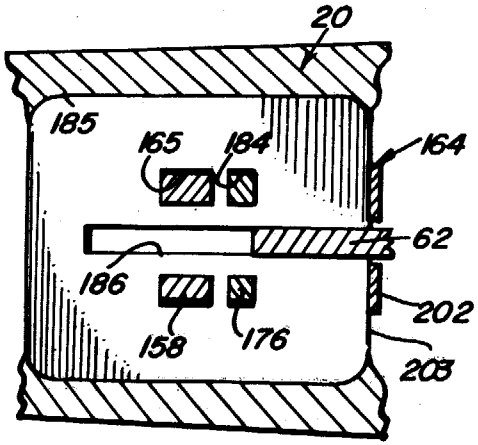
FIG. 18 is a horizontal cross-section taken along line 18—18 of FIG. 1 and showing the location plate for locating the cartridge interlock, cartridge stop lock and pusher-engaging portion of the thrust bar.

FIG. 18 shows a top view of the location plate 164, with thrust bar 30 in its initial position. Location plate 164 is housed in an opening 185 in the forward end 22 of nose portion 20. As previously described, location plate 164 has openings 164 and 184 therein for receiving leg portions 158 and 176 of cartridge interlock 152 and cartridge stop lock 170, respectively. Location plate 164 also has a longitudinally extending opening 186 which receives pusherengaging extension 62 and thereby allows thrust bar 30 to reciprocate.

With reference now to FIGS. 6, 7, 19 and 20, the association of the staple-carrying cartridge 26 with the stapler 10 will be explained. Staple-carrying cartridge 26, as can be seen in the figures, is detachably mounted on nose portion 20. Staple-carrying cartridge 26 is elongated and has a pair of upwardly extending spaced tabs 202 at its rear end. The spacing between tabs 202 is sufficient to allow pusher-engaging extension 62 to freely slide therebetween and tabs 202 are dimensioned and positioned so as to engage surface 203 at rearmost end of location plate 164. Therefore, when tabs 202 engage surface 203, staple-carrying cartridge 26 cannot be inadvertently pulled out of the nose, and cartridge 26 is fixed against forward movement during the stapling operation.

Staple-carrying cartridge 26 is mounted in stapler 10 by inserting the end of cartridge 26 into opening 110 in nose portion 20. The rearward end of staple-carrying cartridge 26 engages a leaf spring 108 which urges the cartridge 26 upwardly until tabs 202 are positively locked into their associated indentations in the body of nose portion 20. With cartridge 26 in this position, the rearward ends 228 of the drive screws 218 forming a part of staple-carrying cartridge 26 are engaged by slots 39 of pinion shafts 38. The cartridge 26 is removed from the stapler 10, when exhausted of staples, by reversing the insertion steps.

With specific reference now to FIGS. 19–22, the construction and operation of the staple-carrying cartridge 26 will be explained. The cartridge 26 is defined by a main body 200 and has an anvil 204 at its forwardmost region projecting out as an extension of the top of cover plate 206. Staple-carrying cartridge 26 houses a plurality of staples 208 whose cross bars 210 lie transverse to the length of cartridge 26 and whose points 212 face anvil 204. A pusher element 214 covers staples 208 and is slidingly mounted within indentations 216 in cover plate 206. Pusher element 214 is adapted to be engaged by pusher-engaging extension 62 of thrust bar 30 and serves both to eject staples 208 from the cartridge 26 and to form the ejected staples around anvil 204.

The means for advancing staples 208 along the length of cartridge 26 comprises a pair of drive screws 218. Screws 218 are provided with threads 220 for guiding and propelling staples 208 along main body ledges 222 between the lateral walls 221. The pusher element 214 is guided between the tops of screws 218 and the bottom of cover plate 206, and serves to hold each of the staples 208 against ledges 222, except during the driving operation. Then, the forwardmost staple 208 is advanced out of the screw guiding threads 220 by means of inclined surfaces 224, at the forward ends of ledges 222, into the plane of pusher element 214, and is propelled forward, out of the main body portion and against anvil 204.

Each screws 218 is provided at its rearwardmost end with an extension 226 fitted at its extremity with a flat projection 228. Screws 218 are threaded so that when they, by means of projections 226 associating with pinion shafts 38 are rotated through 360°, each staple 208 moves one staple unit. A "staple unit" is defined as that distance which is required to move the second staple from its readiness position into a position ready to be fired. Thus, in FIG. 21, one staple unit is shown at a.

Figure 22:
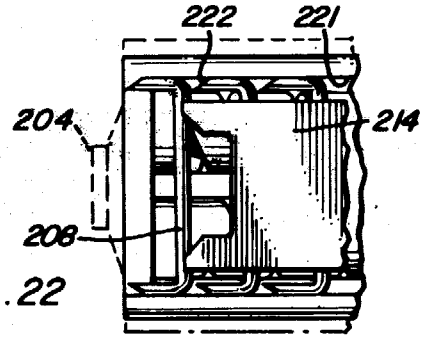
FIG. 22 is a view of the front portion of the cartridge during the stapling operation, with the cover removed.

In operation, while pusher element 214 is moving forward by thrust bar 30, and after the forwardmost staple has been raised into the plane of the pusher, pusher element 214 makes contact with the staple as illustrated in FIG. 22. Then, the staple is ejected and formed in the disunited skin or fascia of the patient as is more fully described in the above-referenced commonly assigned patents, the pertinent disclosures of which are expressly incorporated herein by reference.

Above there have been described specific embodiments of the present invention. It should be noted, however, that the above description was given for illustrative purposes only and that many alterations and modifications may be practiced by those skilled in the art without departing from the spirit or the scope of the present invention. It is the intent therefore that the present invention not be limited to the above but be limited only as defined in the appended claims.

What is claimed is:

1. A surgical stapling instrument for applying sterilized staples to the disunited skin or fascia of a patient for effecting a joining of the skin or fascia, the instrument adapted to associate with a staple-carrying cartridge having anvil means at one end thereof and adapted to house a plurality of staples therein, a pusher element slidably mounted therein for ejecting staples from said cartridge and for forming said staples around said anvil means, and means for advancing said staples in said cartridge, said surgical stapling instrument comprising: a main body portion; means for mounting said staple-carrying cartridge on said main body portion; drive means to activate said staple-advancing means for driving the staples toward said anvil means [; ] and [ pusher-activating means ] for driving the pusher element forward to eject a staple from the staple-carrying cartridge and to form said staple around said anvil means; said instrument being manually powered, and further comprising trigger means for transmitting a manually applied force to said drive means [ and said pusher-activating means ] to power said drive means [ and said pusher-activating means ].

2. The instrument defined in claim 1, wherein said [ pusher-activating ] *drive* means comprises a thrust bar slidably mounted in said main body portion and said trigger means comprises a handle pivotally mounted to said main body portion and having a lower hand-engaging portion and an upper force-transmitting portion associated with said thrust bar.

3. The instrument defined in claim 2, wherein means are associated with said thrust bar for initiating the advancement of staples, said initiating means comprising an index pawl pivotally mounted to said thrust bar and adapted for sliding movement therewith.

4. The instrument defined in claim 3, wherein said thrust bar has a notch formed therein and wherein said index pawl has an upstanding leg formed thereon and cooperating with said notch to permit the pivotal movement of said index pawl, and wherein said index pawl is pivotally mounted to said thrust bar by means of a resilient member.

5. The instrument defined in claim 1, wherein said drive means comprises a ratchet and main gear mounted in said main body portion for rotation in unison, at least one pinion gear rotatably driven by said main gear, and a pinion shaft rotatably driven by each said pinion gear.

6. The instrument defined in claim 5, wherein said drive means is adapted to be over-driven and thereby advance each staple but the first in said staple-carrying cartridge more than one staple unit for each thrust of said thrust bar; and further including means to reverse the direction of rotation of said drive means so that said drive means ultimately advances each staple one staple unit, said reversing means comprising a spring pawl biasing said drive means in said reverse directon when said drive means is in the over-driven state.

7. The instrument defined in claim 1, and further comprising means for alerting the surgeon that a staple has reached a readiness position for ejection and formation.

8. The instrument defined in claim 7, wherein said alerting means comprises a notch associated with said pusher-activating means and a spring-biased wedge housed in said main body portion and adapted to cooperate with said notch to provide said alerting function.

9. A surgical stapling instrument for applying sterilized staples to the disunited skin or fascia of a patient for effecting a joining of the skin or fascia, the instrument adapted to associate with a staple-carrying cartridge having anvil means at one end thereof and adapted to house a plurality of staples therein, a pusher element slidably mounted therein for ejecting staples from said cartridge and for forming said staples around said anvil means, and means for advancing said staples in said cartridge, said surgical stapling instrument comprising: a main body portion; a nose portion; means for mounting said staple-carrying cartridge on said nose portion so that said cartridge is rotatable therewith; drive means housed in said nose portion and rotatable therewith for activating said staple-advancing means for driving the staples toward said anvil means [ ; ] and [ pusher-activating means housed in said nose portion and rotatable therewith ] for driving the pusher element forward to eject a staple from the staple-carrying cartridge and to form said staple around said anvil means, wherein said instrument is manually powered, and further comprising trigger means for transmitting a manually applied force to said drive means [ and said pusher-activating means ] to power said drive means [ and said pusher-activating means ].

10. The instrument defined in claim 9, wherein said [ pusher-activating ] *drive* means comprises a thrust bar slidably mount in said nose portion and said trigger means comprises a handle pivotally mounted to said main body portion and having a lower hand-engaging portion and an upper force-transmitting portion, and wherein said instrument further comprises collar means housed in said main body portion and slidably mounted on and rotatable with said nose portion for transmitting force from said trigger means to said [ pusher-activated ] *drive* means.

11. The instrument defined in claim 10, wherein said collar means comprises a cylindrically-shaped body member having outwardly and radially extending flange portions at each end thereof, and wherein said upper force-transmitting portion of said trigger means is formed in the shape of a yoke and is positioned around said cylindrically-shaped body member and between said flange portions of said collar means so that said collar means can rotate relative to said trigger means.

12. A surgical stapling instrument for applying sterilized staples to the disunited skin or fascia of a patient for effecting a joining of the skin or fascia, the instrument adapted to associate with a staple-carrying cartridge having anvil means at one end thereof and adapted to house a plurality of staples therein, a pusher element slidably mounted therein for ejecting staples from said cartridge and for forming said staples around said anvil means, and means for advancing said staples in said cartridge, said surgical staple instrument comprising: a main body portion; means for mounting said staple-carrying cartridge on said main body portion; drive means to activate said staple-advancing means for driving the staples toward said anvil means [ ; pusher-activating means ] *and* for driving the pusher element forward to eject a staple from the staple-carrying cartridge and to form said staple around said anvil means; and clutch means for preventing said drive means from activating said staple-advancing means more than once in each stapling operation, said clutch means comprising two surfaces movable relative to one another with one of said two surfaces being sloped relative to the other, a roller positioned between said two surfaces, and a wedge member in one of said two surfaces, said wedge member adapted to permit said roller means to move therepast only at the respective ends of the drive means stroke.

13. The instrument defined in claim 12, wherein said [ pusher-activating ] *drive* means comprises a thrust bar slidingly mounted for reciprocative movement in said main body portion and wherein said clutch means prevents said thrust bar from returning to its initial rest position until said thrust bar has completed its forward thrust movement.

14. The instrument defined in claim 13, wherein the sloped surface is inclined relative to said thrust bar and defines an opening therewith which increases in size in the direction of the forward thrust movement of said thrust bar, and wherein said roller is positioned between and cooperating with said sloped surface and said thrust bar.

15. The instrument defined in claim 14, wherein said wedge member cooperating with said roller is spring-biased.

16. A surgical stapling instrument for applying sterilized staples to the disunited skin or fascia of a patient for effecting a joining of the skin or fascia, the instrument adapted to associate with a staple-carrying cartridge having anvil means at one end thereof and adapted to house a plurality of staples therein, a pusher element slidably mounted therein for ejecting staples from said cartridge and for forming said staples around said anvil means, and means for advancing said staples in said cartridge, said surgical stapling instrument comprising: a main body portion; means for mounting said staple-carrying cartridge on said main body portion: drive means to activate said staple-advancing means for driving the staples toward said anvil means [ ; pusher-activating means ] *and* for driving the pusher element forward to eject a staple from the staple-carrying cartridge and to form said staple around said anvil means; and locking means associated with said [ pusher-activating ] *drive* means and adapted to cooperate with said staple-carrying cartridge for ensuring that said [ pusher-activating ] *drive* means is in its initial rest position when said staple-carrying cartridge is mounted on said main body portion.

17. The instrument defined in claim 16, wherein said locking means is adapted to lock said [ pusher-activating ] *drive* means in its initial rest position until said staple-carrying cartridge is mounted on said main body portion.

18. The instrument defined in claim 17, wherein said [ pusher-activating ] *drive* means comprises a thrust bar mounted for reciprocative movement in said main body portion, and wherein said locking means comprises a movable cartridge interlock member adapted to lie in blocking and abutting relationship with the forwardmost end of said thrust bar when said thrust bar is in its initial rest position and adapted to move out of said blocking relationship with said thrust bar when said staple-carrying cartridge is mounted on said main body portion.

19. The instrument defined in claim 18, wherein said cartridge interlock member comprises a body portion spring-biased toward a blocking relationship with said thrust bar and having an opening therein through which said thrust bar can pass when moved out of said blocking relationship, said cartridge inter-lock member further having a leg porton adapted to contact said staple-carrying cartridge when said staple-carrying cartridge is mounted on said main body portion such that said cartridge inter-lock member is moved out of said blocking relationship.

20. The instrument defined in claim 16, wherein said locking means comprises a movable cartridge stop lock member adapted to prevent the mounting of said staple-carrying cartridge in said main body portion unless said [ pusher-activating ] *drive* means is in said initial rest position.

21. The instrument defined in claim 20, wherein said [ pusher-activating ] *drive* means comprises a thrust bar mounted for reciprocative movement in said main body portion and wherein said cartrige stop lock member is adapted to block the mounting of said staple-carrying cartridge when said thrust bar is not in said initial rest position, and is adapted to be moved into a non-blocking position by said thrust bar when said thrust bar is in said initial rest position.

22. The instrument defined in claim 20, wherein said cartridge stop lock member comprises a body portion and a leg portion, said leg portion being spring-biased into a position adapted to block the mounting of said staple-carrying cartridge when said thrust bar is not in said initial rest position, and wherein each of said cartridge stop lock member and said thrust bar have correspondingly inclined surfaces such that said cartridge stop lock member is moved into a non-blocking position by said thrust bar when said thrust bar is in said initial rest position.

* * * * *